United States Patent [19]

Bricker

[11] Patent Number: 4,691,071

[45] Date of Patent: Sep. 1, 1987

[54] DEHYDROGENATION OF DEHYDROGENATABLE HYDROCARBONS

[75] Inventor: Jeffery C. Bricker, Buffalo Grove, Ill.

[73] Assignee: UOP Inc., Des Plaines, Ill.

[21] Appl. No.: 940,665

[22] Filed: Dec. 11, 1986

[51] Int. Cl.$^4$ .............................................. C07C 1/00
[52] U.S. Cl. ................................. 585/319; 585/443; 585/444
[58] Field of Search ...................... 585/319, 443, 444

[56] References Cited

U.S. PATENT DOCUMENTS

| | | | |
|---|---|---|---|
| 3,380,931 | 4/1968 | Ryland | 252/432 |
| 3,437,703 | 4/1969 | Reitmeier et al. | 260/669 |
| 3,670,044 | 6/1972 | Drehman et al. | 260/683.3 |
| 3,855,330 | 12/1974 | Mendelsohn et al. | 260/669 R |
| 4,435,607 | 3/1984 | Imai | 585/443 |
| 4,565,898 | 1/1986 | O'Hara et al. | 585/319 |

Primary Examiner—Curtis R. Davis
Attorney, Agent, or Firm—Thomas K. McBride; John F. Spears, Jr.; Raymond H. Nelson

[57] ABSTRACT

Dehydrogenatable hydrocarbons may be subjected to a dehydrogenation reaction by treating the hydrocarbons in the presence of a dehydrogenation catalyst comprising an alkaline metal-promoted iron compound. The effluent is then subjected to a selective oxidation step in which the hydrogenation produced from the first reaction is oxidized in preference to the dehydrogenated and unconverted hydrocarbons. The catalyst which is used to effect this selective oxidation comprises a Group VIII noble metal, a Group IVA metal and a Group IA or IIA metal composited on a metal oxide support. The present invention is concerned with the use of a cerium-containing alumina as a support for this selective oxidation catalyst.

19 Claims, No Drawings 4,691,071

DEHYDROGENATION OF DEHYDROGENATABLE HYDROCARBONS

BACKGROUND OF THE INVENTION

It has been known in the prior art that unsaturated hydrocarbons may be obtained from the dehydrogenation of dehydrogenatable hydrocarbons. The dehydrogenation may be effected by subjecting the dehydrogenatable hydrocarbons to a dehydrogenation process at dehydrogenation conditions in the presence of certain catalytic compositions of matter which possess the ability to dehydrogenate said compounds with the resultant formation of olefinic hydrocarbons. The particular dehydrogenation catalysts which are employed are well known in the art and comprise such compounds as nickel composited on a solid support such as diatomaceous earth, kieselguhr, charcoal and iron composited on the same supports, etc.

Other dehydrogenation processes have employed, in addition to the dehydrogenation catalysts, an oxidation catalyst in the reaction process. The presence of the oxidation catalyst is necessitated by the fact that it is advantageous to oxidize the hydrogen which is produced by contact with an oxygen-containing gas in order to maintain the desired reaction temperature. For example, styrene, which is an important chemical compound utilized for the preparation of polystyrene, plastics, resins or synthetic elastomers such as styrene-butadiene rubber, etc., may be prepared from the dehydrogenation of ethylbenzene. The dehydrogenation of ethylbenzene into styrene, which is effected by treating ethylbenzene with steam in the presence of a modified iron catalyst, is endothermic in nature. The heat of reaction is about 30 Kcal per mole of ethylbenzene. Therefore, the temperature of the catalyst bed decreases significantly during the progress of the reaction in a commercial adiabatic reactor resulting in limitation of ethylbenzene conversion to a low level. The limitation of conversion arises from the fact that the equilibrium conversion of ethylbenzene is lowered and the rate of ethylbenzene dehydrogenation decreases as the reaction temperature decreases. The decrease of temperature adversely affects not only the conversion level, but also the selectivity for styrene, since at equilibrium conditions, only undesirable side reactions continue to take place. Therefore, it is necessary to maintain the desired temperature level in order to provide a high equilibrium conversion level and a high reaction rate. In the conventional process, the maintenance of temperature is attained by reheating the product stream with the addition of superheated steam between dehydrogenation catalyst beds using a multicatalyst bed reactor system. However, consumption of the additional superheated steam is considerably high and makes the dehydrogenation process costly. Accordingly, significant process economic improvements over the conventional ethylbenzene dehydrogenation processes can be achieved if the reaction temperature is somehow maintained while eliminating or reducing the additional superheated steam. One method of providing for the maintenance of the reaction temperature is to introduce oxygen into the reaction mixture by way of oxygen or an oxygen-containing gas such as air which will burn the hydrogen formed during the dehydrogenation reaction, this combustion resulting in an exothermic reaction which will provide the necessary amount of heat and, in addition, will shift the equilibrium toward production of styrene since the hydrogen formed in the dehydrogenation is consumed. Consequently, a higher conversion and high styrene selectivity are achievable.

The combustion of hydrogen with the oxygen in the oxygencontaining gas requires the presence of an oxidation catalyst. There are some key requirements for the oxidation catalyst to be useable for such a purpose. The most important catalytic property required is good catalytic stability since the oxidation catalyst must survive under very severe reaction conditions, namely at about 600° to 650° C. in the presence of steam. Under such conditions, porous inorganic materials such as aluminas, silicas and zeolites cannot maintain their pore structures for a long period of time, resulting in the permanent damage of catalysts prepared using such materials as supports, e.g., platinum supported on a porous high surface area alumina, silica, or zeolite. Secondly, the oxidation catalyst must be very active to achieve complete conversion of oxygen to avoid poisoning of iron-based dehydrogenation catalysts which are sensitively oxidized with oxygen to lose their dehydrogenation activities. Thirdly, the oxidation catalyst must be selective for oxidation of hydrogen. Otherwise, ethylbenzene and styrene are consumed to lower the efficiency of styrene productions.

Various U.S. patents have described types of oxidation catalysts which may be employed in this process. For example, U.S. Pat. No. 3,437,703 describes a catalytic dehydrogenation process which employs, as a dehydrogenation catalyst, a composition known in the trade as Shell-105 which consists of from 87% to 90% ferric oxide, 2% to 3% chromium oxide, and from 8% to 10% of potassium oxide. In addition, another dehydrogenation catalyst which is employed comprises a mixture of nickel, calcium, chromic oxide and graphite with a major portion of a phosphate species. In addition to these dehydrogenation catalysts, the reaction also employs a catalyst for the oxidation step of the process comprising platinum or palladium in elemental form or as a soluble salt. Another U.S. patent, namely U.S. Pat. No. 3,380,931, also discloses an oxidation catalyst which may be used in the oxidative dehydrogenation of compounds such as ethylbenzene to form styrene comprising an oxide of bismuth and an oxide of a metal of Group VIB of the Periodic Table such as molybdenum oxide, tungsten oxide or chromium oxide. In addition, the patent also states that minor amounts of arsenic may also be present in the catalytic composite as well as other metal or metalloids such as lead, silver, tin, manganese, phosphorus, silicon, boron and sulfur.

U.S. Pat. No. 3,855,330 discloses a method for the production of styrene in which ethylbenzene is treated in the vapor state by passage over a dehydrogenation catalyst and an oxidation catalyst while introducing oxygen into the reaction medium. The dehydrogenation catalysts which are employed are those which have been set forth in various prior U.S. patents and which may be similar in nature to the dehydrogenation catalysts previously discussed. The types of oxidation catalysts which may be employed will include platinum or palladium catalysts which are composited on alumina or molecular sieves zeolite-type which have been charged with ferrous, heavy or noble metals. The patent lists the types of catalysts which are employed including copper or various zeolites, platinum on alumina, platinum on spinel, platinum and sodium on zeolites, platinum, sodium and potassium on zeolites, etc.

U.S. Pat. No. 3,670,044 discloses a method for dehydrogenating cycloalkane, arylalkane and alkanes in the presence of gaseous hydrogen or mixture of gaseous hydrogen and gaseous oxygen using a catalyst composition comprising a Group VIII metal or a mixture of a Group VIII metal and a Group IVA metal deposited on a support comprising a Group II aluminate spinel. It is noted that the patentee teaches that added hydrogen is used in connection with the oxygen, and that when only oxygen is used, the conversion and selectivity are generally low. The addition of hydrogen is believed to be a significant disadvantage in the dehydrogenation process inasmuch as the equilibrium conversion is lowered. This is in contradistinction to the process of the present invention wherein the dehydrogenation process, prior to the oxidation step, is not effected in the presence of any added hydrogen. As will hereinafter be shown in greater detail, the present process results in the selective oxidation of hydrogen with a concomitantly lower selectivity to carbon monoxide and carbon dioxide. In addition, the patentee teaches the use of one catalyst for both dehydrogenation and oxidation which is in contrast to the separate dehydrogenation and oxidation catalysts which are used in the present process.

In addition to the aforementioned U.S. patents, another patent, namely U.S. Pat. No. 4,435,607, also discloses a method for the dehydrogenation of dehydrogenatable hydrocarbons utilizing a two-step process which includes dehydrogenation followed by a selective oxidation process. The catalyst which is employed for the selective oxidation will comprise a noble metal of Group VIII, a metal of Group IVA and, if so desired, a metal of Group IA or IIA of the Periodic Table composited on a highly porous inorganic support. The catalyst base which is used to prepare the oxidation catalyst in this patent was prepared from particles which were relatively small in size.

However, as will hereinafter be shown in greater detail, it is possible to obtain a high selectivity to desired products with a concurrent catalyst stability by utilizing, as a support for the metallic portions of the selective oxidation catalyst, a particular combination of a metal oxide and cerium.

BRIEF SUMMARY OF THE INVENTION

This invention relates to a process for the dehydrogenation of dehydrogenatable hydrocarbons. More specifically, the invention is concerned with a process for the dehydrogenation of a dehydrogenatable hydrocarbon in which the hydrocarbon which is to undergo treatment is subjected to a dehydrogenation step in the presence of a dehydrogenation catalyst. This dehydrogenation step is followed by a selective oxidation step in which the product mixture which results from the aforementioned dehydrogenation step is treated in the presence of certain catalytic compositions of matter which are hereinafter set forth in greater detail in such a manner whereby the hydrogen which is present and which has resulted from the dehydrogenation step is selectively oxidized with a concomitant minimum oxidation of the hydrocarbons. By utilizing the particular support for the selective oxidation catalyst, it is possible to obtain the desired dehydrogenated hydrocarbons in a relatively high yield as well as maintaining the stability and activity of the catalyst to a greater degree than has heretofore been experienced. By maintaining the aforementioned stability and activity, it is possible to obviate the necessity for relatively frequent changes of the catalyst or, in the alternative, regenerating the catalyst, thereby adding to the commercial attractiveness and economical feasibility of the dehydrogenation process.

It is therefore an object of this invention to provide a process for the dehydrogenation of dehydrogenatable hydrocarbons.

A further object of this invention is to provide a catalyst for the selective oxidation step of the process whereby hydrogen which is formed during the dehydrogenation process will be selectively oxidized to the substantial exclusion of the oxidation of the hydrocarbons.

In one aspect, an embodiment of this invention resides in a process for the dehydrogenation of a dehydrogenatable hydrocarbon with separate and intermediate selective oxidation of hydrogen which comprises the steps of: (a) contacting said hydrocarbon with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of unconverted hydrocarbons, dehydrogenated hydrocarbons, hydrogen and steam; (b) removing said first-reaction dehydrogenation zone effluent from said first-reaction dehydrogenation zone; (c) passing said effluent of step (b) to a second-reaction oxidation zone, which is separate and discrete from said first-reaction dehydrogenation zone; (d) contacting said first-reaction dehydrogenation zone effluent in said second-reaction oxidation zone with an oxygen-containing gas to selectively oxidize said hydrogen within said first-reaction zone effluent to the substantial exclusion of oxidation of unconverted and dehydrogenated hydrocarbons in the presence of an oxidation catalyst consisting essentially of a Group VIII noble metal, a Group IVA metal and a Group IA or IIA metal composited on a metal oxide support at oxidation conditions wherein the exothermic selective oxidation of said hydrogen provides additional heat and thereby raises the temperature of said unconverted and dehydrogenated hydrocarbons; (e) withdrawing said unconverted and dehydrogenated hydrocarbons from said second-reaction oxidation zone having an increased temperature with respect to the temperature of said first-reaction dehydrogenation zone effluent; (f) passing said removed second-reaction oxidation zone product stream of step (e) to a third-reaction dehydrogenation zone containing a dehydrogenation catalyst comprising an alkaline metal-promoted iron compound at dehydrogenation conditions to produce dehydrogenated hydrocarbons; and, (g) withdrawing and recovering said dehydrogenated hydrocarbons, the improvement which comprises utilizing as said support a cerium-containing alumina.

A specific embodiment of this invention is found in a process for the dehydrogenation of ethylbenzene which comprises contacting said ethylbenzene with a dehydrogenation catalyst comprising an alkaline metal-modified iron catalyst at a temperature in the range of from about 500° to about 700° C. and a pressure in the range of from about 1 to about 10 atmospheres (0.1013 to 10.133 kPa) in the presence of steam, thereafter contacting the resultant mixture of unconverted ethylbenzene, styrene, hydrogen and steam with air at a temperature in the range of from about 500° to about 700° C. and a pressure in the range of from about 0.1 to about 10 atmospheres (0.1013 to 10.133 kPa) in the presence of a catalyst comprising a mixture of platinum, tin and lithium composited on a support comprising a cerium-containing alumina, whereby hydrogen is selectively oxidized to the substantial exclusion of oxidation of unconverted ethylbenzene and styrene, and recovering the desired styrene after the final stage of dehydrogenation.

Other objects and embodiments will be found in the further detailed description of the invention.

DETAILED DESCRIPTION OF THE INVENTION

As hereinbefore set forth, the present invention is concerned with a dehydrogenation process for the dehydrogenation of dehydrogenatable hydrocarbons which involves the use, in one step of the process, of a selective oxidation catalyst which will provide improved stability and effectiveness of the active elements as well as eliminating some disadvantages which have been present when prior catalytic compositions of matter have been used in the same process. The particular selective oxidation catalyst which is used in the process of the present invention comprises a noble metal of Group VIII of the Periodic Table, a Group IVA metal of the Periodic Table and a metal of Group IA or IIA of the Periodic Table composited on a solid porous inorganic metal oxide support. In the preferred embodiment of the invention, the inorganic metal oxide support will comprise an alumina such as an alpha-alumina or a mixture of alpha-alumina and theta-alumina. In the process of the present invention, this inorganic metal oxide support will be composited or will contain cerium. The incorporation of cerium into the selective oxidation catalyst may be accomplished by a number of techniques. The cerium may be added during the support forming step, which may consist of extrusion, oil-dropping, pelletizing, co-mulling, and binding with certain binders. Alternatively, the cerium may be added to the support after the support forming step by means of impregnation of a soluble salt such as cerium nitrate, cerium oxalate, cerium acetate, and cerium chloride. The cerium may also be added by co-impregnation with other metallic components of the selective oxidation catalyst. The cerium which, after calcination of the alumina support or catalyst, will exist primarily as a cerium oxide. The incorporation of the cerium into the support lattice of the porous inorganic metal oxide support will increase the stability of the selective oxidation catalyst by allowing the catalyst to maintain high activity for catalyzing the desired reaction, which is the selective oxidation of hydrogen. Therefore, the selective oxidation catalyst which utilizes this type of support will provide an improved catalyst performance with respect to the ability of the catalyst to provide the selective oxidation of hydrogen to the substantial exclusion of the oxidation of the hydrocarbons, both unconverted and converted which are present in the effluent emanating from a dehydrogenation zone.

In the present process, a dehydrogenatable hydrocarbon of the type hereinafter set forth in greater detail is contacted with a dehydrogenation catalyst in the presence of steam in a multicatalyst bed system. Inasauch as the dehydrogenation of the hydrocarbon is endothermic in nature, it is necessary to provide an additional amount of heat before the product enters the next catalyst bed in order to provide a high equilibrium conversion as well as a high reaction rate. One method of effecting this increase in the desired temperature is to provide an internal catalytic combustion of the hydrogen which is produced during the dehydrogenation reaction in order to reheat the product to the desired level. By effecting a selective oxidation of the hydrogen, it is possible to avoid the use of superheated steam or other outside sources of heat. This selective oxidation of hydrogen with the resultant composition thereof is effected by utilizing a selective oxidation catalyst of the type hereinafter set forth in greater detail, the selective oxidation catalyst maintaining its stability and activity for a considerable length of time.

The process of the present invention may be effected by utilizing an apparatus in which the dehydrogenation catalyst and the oxidation catalyst, both of the type hereinafter set forth in greater detail, are loaded in the apparatus in alternate layers. The number of alternate layers of dehydrogenation catalyst and selective oxidation catalyst may vary according to the size or type of apparatus which is employed, the number of alternate layers ranging from three to about nine. As will hereinafter be shown, the dehydrogenation catalyst and the oxidation catalyst are different in nature. Examples of dehydrogenation catalysts which may be employed will comprise an alkaline earth metal-promoted iron compound. The term "alkaline metal" as used in the present specification and appended claims will refer to metals of Groups IA and IIA of the Periodic Table which include lithium, sodium, potassium, rubidium, cesium, beryllium, magnesium, calcium, strontium and barium. In addition, the promoted iron compound catalyst will, in the preferred embodiment of the invention, also include a compound containing a metal of Groups IVB, VB and VIB of the Periodic Table. For example, a typical dehydrogenation catalyst which may be employed in the process of this invention will consist essentially of about 85% by weight of ferric oxide, 12% by weight of potassium hydroxide, 2% by weight of chromia and 1% by weight of sodium hydroxide. Another typical dehydrogenation catalyst which may be used comprises 90% by weight of ferric oxide, 4% by weight of chromia and 6% by weight of potassium carbonate. In addition to these catalysts, other well-known dehydrogenation catalysts which may be utilized will include those comprising ferric oxide, potassium oxide, as well as other metal oxides and/or IIA, IVB, VB and VIB of the Periodic Table including those of calcium, lithium, strontium, magnesium, beryllium, zirconium, tungsten, molybdenum, hafnium, vanadium, copper, chromium and mixtures of two or more oxides such as chromia-alumina, chromia-titania, alumina-vanadia and the like.

The dehydrogenation of a dehydrogenatable hydrocarbon such as, for example, ethylbenzene, is effected by contacting the dehydrogenatable hydrocarbon and steam, in the absence of any added hydrogen, with the aforesaid catalyst at dehydrogenation conditions which are in the range of from about 500° to about 700° C. and at a reaction pressure in the range of from about 0.1 to about 10 atmospheres (0.1013 to 10.133 kPa); the exact dehydrogenation conditions are, however, a function of the particular dehydrogenatable hydrocarbon undergoing dehydrogenation. Other reaction conditions will include a Liquid Hourly Space Velocity based on the hydrocarbon charge of from about 0.1 to about 10 hrs$^{-1}$ and steam to hydrocarbon weight ratios ranging from about 1:1 to about 40:1. The number of dehydrogenation zones of the catalyst beds may vary from 1 to about 5 in number and typically may comprise three reaction zones; however, the number of zones is not critical to the invention. After contacting the dehydrogenation catalyst with the steam and hydrocarbon, the resulting mixture comprising unconverted hydrocarbon, dehydrogenated hydrocarbon, steam and hydrogen which has passed through the catalyst bed is contacted in a separate zone with the selective oxidative catalytic composition of the type hereinafter set forth in greater detail. In addition, oxygen-containing gas is introduced into the reactor, preferably at a point adjacent to the oxidation catalyst bed. Examples of oxygen-containing gases which may be utilized to effect the selective oxidation of the hydrogen which is present will include air, oxygen, air or oxygen diluted with other gases such as steam, carbon dioxide and inert gases such as nitrogen, argon, helium, etc. The amount of oxygen which is introduced to contact the product stream may range from about 0.1:1 to about 2:1 moles of oxygen per mole of hydrogen contained in the product stream. In this particular reaction zone, the product stream, which comprises unreacted dehydrogenatable hydrocarbon, dehydrogenated hydrocarbon, hydrogen and steam, undergoes a selective oxidation in contact with oxygen and the oxidative catalyst whereby hydrogen is selectively oxidized to water with a minimal amount of reaction of oxygen with the hydrocarbons, either unconverted hydrocarbon or dehydrogenated hydrocarbon.

After passage through the zone containing the oxidation catalyst, the mixture may then be passed through a second dehydrogenation zone containing a dehydrogenation catalyst of the type hereinbefore set forth for further dehydrogenation, the process being completed through the plurality of zones followed by withdrawal of the product stream and separation of the unconverted hydrocarbon from the desired dehydrogenated product.

It is contemplated that the dehydrogenation process for the dehydrogenation of dehydrogenatable hydrocarbons utilizing the oxidative catalytic compositions of matter of the present invention will be applicable to a wide variety of dehydrogenatable hydrocarbons. Examples of hydrocarbons which are susceptible to a dehydrogenation process utilizing the catalysts of the present invention will include lower alkyl-substituted aromatic hydrocarbons such as ethylbenzene, diethylbenzene, isopropylbenzene, diisopropylbenzene, o-ethyltoluene, m-ethyltoluene, p-ethyltoluene, o-isopropyltoluene, m-isopropyltoluene, p-isopropyltoluene, ethylnaphthalene, propylnapththalene, isopropylnaphthalene, diethylnaphthalene, etc., paraffins such as ethane, propane, n-butane, isobutane, n-pentane, isopentane, n-hexane, n-heptane, n-octane, n-nonane, n-decane, and branched chain isomers thereof, cycloparaffins such as cyclobutane, cyclopentane, cyclohexane, methylcyclopentane, methylcyclohexane, ethylcyclopentane, olefins such as ethylene, propylene, 1-butene, 2-butene, 1-pentene, 2-pentene, 1-hexene, 2-hexene, 3-hexene, and branched chain derivatives thereof, etc.

The selective oxidation step of the process utilizes, as hereinbefore set forth, the hydrogen which has been produced in the dehydrogenation step of the process to supply heat to the inlet of the next dehydrogenation catalyst bed. Inasmuch as temperatures which are utilized in the process may be as high as 650° C. in the presence of steam, the operating conditions in which the oxidation catalyst must function are severe in nature. In order for the oxidation catalyst to remain stable and minimize the carbon formation thereon, the catalyst support must be calcined at a relatively high temperature in order to decrease the surface area, this decrease in surface area contributing to the stability of the catalyst. Conventional oxidation catalysts utilizing a porous support such as alumina which had been calcined at relatively low temperatures, i.e., below about 900° C. or lower, lose surface area at a rapid rate and form excessive carbon on the surface thereof, thus resulting in a deactivation of the catalyst.

An effective oxidation catalyst which may be used in the dehydrogenation and selective oxidation process of the present invention comprises a noble metal of Group VIII of the Periodic Table such as platinum along with a Group IVA metal of the Periodic Table such as tin and, if so desired, a metal selected from Group IA and IIA of the Periodic Table composited on a solid porous inorganic oxide support.

The solid porous inorganic oxide support will comprise, as hereinbefore set forth, an alumina which contains a cerium compound. The final support for the catalytic metals of the composite will possess the necessary stability to effectively operate as an efficient catalyst over a relatively long period of time while maintaining the ability to selectively oxidize hydrogen which is obtained from the dehydrogenation step of the process. As an example, the alumina which comprises one component of the support will be derived from the various types of aluminas such as, for example, boehmite, pseudoboehmite, gibbsite, etc. By utilizing such a precursor, it is possible after peptizing of the precursor and calcination, to obtain a finished catalyst support which will provide the enhanced stability which is desired to be present in the final catalyst composite. The calcination of the support is effected at a temperature within the range of from about 900° to about 1500° C. prior to impregnation of the metals thereon. If so desired, the calcination of this support may be effected in a dry atmosphere, preferably at a temperature in the range of from about 1100° to about 1500° C. or the calcination may be effected in a hydrous atmosphere such as that provided by steam, the temperatures preferably in the range of from about 900° to about 1200° C. The calcination of the support within these temperature ranges will be effected over a period of time which may range from about 0.5 to about 30 hours or more in duration and it is to be understood that the particular temperature which is selected for the calcination of the support will influence or direct the time frame during which the calcination takes place.

The alumina support which is recovered from the calcination step will, in the preferred embodiment of the invention, possess certain desirable characteristics or properties. For example, the ABD of the finished support will preferably be in a range of from about 0.3 to about 1.1 g/cc, the pore volume greater than about 0.2 cc/g, the surface area in a range of from about 1 to about 80 m$^2$/g. The particle size of the alumina support which is obtained will be relatively large. For example, particles which may be obtained by extruding this material will possess diameters in a range of from about 1 to about 15 mm, preferably in a range of from about 1.5 to about 8 mm, and may have a length in a range of from about 2 to about 50 mm, preferably in a range of from about 4 to about 18 mm. If the alumina support is not extruded but obtained by other means such as oil drop methods, it is possible to obtain particles in the shape of spheres which possess diameters in the range of from about 1.5 mm to about 20 mm, and preferably in a range of from about 1.8 to about 10 mm. In addition, the alumina may be present as alpha-alumina or as a mixture of alpha-alumina and theta-alumina.

As will hereinafter be shown in greater detail, the use of a support possessing the properties and sizes will result in the obtention of a catalyst composite which will exhibit greater stability and selectivity as well as a lower pressure drop when employed in the selective oxidation process than will be found when utilizing catalyst supports which possess properties and particle sizes outside the range set forth for the low density alumina precursors.

In one embodiment of the present invention, the alumina precursor will have incorporated therein a cerium compound such as cerium acetate, cerium nitrate, cerium carbonate, cerium bromate, cerium bromide, cerium oxalate, etc. The alumina precursor, which may be in the form of a powder, is added to an aqueous solution of the cerium compound during the support forming step. Following this, the cerium-containing alumina composite may then be treated in the manner hereinbefore set forth by drying and calcination within the ranges previously mentioned to form the desired support. The cerium which, after calcination of the alumina support, will exist as a cerium oxide will be present in the support in an amount in the range of from about 0.01% to about 5.0% by weight of the support composite.

As was hereinbefore set forth, the selective oxidation catalysts which are employed in the process of this invention will comprise a noble metal of Group VIII of the Periodic Table and a metal of Group IVA of the Periodic Table composited on a solid inorganic support which, prior to the compositing of the metals thereon, has been peptized and thereafter calcined at a temperature within the range hereinbefore discussed. In addition, if so desired, it is also contemplated within the scope of this invention that the catalyst will also contain a metal selected from Groups IA and IIA of the Periodic Table. Of the noble metals of Group VIII of the Periodic Table, platinum, palladium and rhodium comprise the preferred species, said metals being present in the final composite in an amount in the range of from about 0.01% to about 5% by weight. Of the metals of Group IVA of the Periodic Table, germanium, tin and lead comprise the preferred species, these metals also being present in the final catalyst composite in an amount in the range of from about 0.01% to about 5% by weight. The preferred species of metals of Group IA or IIA of the Periodic Table will include lithium, sodium, potassium, rubidium, cesium, beryllium, magnesium, calcium, barium, francium, and radium, the alkali metals or alkaline earth metals being present in an amount in the range of from about 0.01% to about 10% by weight of the catalyst composite.

The selective oxidation catalyst which utilizes, as the support for the metallic portion of the composite, an alumina which possesses the desired properties hereinbefore set forth, may be prepared in any suitable manner known in the art. For example, one type of preparation will comprise impregnating a solid support previously described, and which may be in the form of beads, spheres, pellets, etc., with an aqueous or acidic solution of a Group VIII metal compound of the Periodic Table. The form in which the support is used may have been prepared by various methods such as particles prepared by oil dropping, extrusion, pelletizing and binding with certain binders. The aqueous solution of the noble metal-containing compound may be prepared from soluble salts of these metals, such as chloroplatinic acid, chloropalladic acid, rhodium chloride, platinum sulfate, palladium sulfate, etc. The solid support is impregnated with the solution for a period of time which is sufficient to allow the deposition of the desired amount of the noble metal on the solid support, that is, an amount sufficient so that the finished catalytic composition will contain from about 0.01% to about 5% by weight of the composite. After recovery of the impregnated solid support, the composite is then dried and calcined at a temperature in the range of from about 500° to about 600° C. or more in an air or air/steam atmosphere.

The thus formed composite containing a noble metal may then be further impregnated with an aqueous solution of a metal of Group IVA of the Periodic Table. In a similar manner to that hereinbefore described, the amount of soluble salts such as tin chloride, tin bromide, tin sulfate, lead chloride, lead persulfate, germanium chloride, etc. will be present in the solution sufficient so that the finished catalytic composition will contain the desired amount of metals. Again, the impregnation is allowed to proceed for a predetermined period of time following which the composite is recovered, dried and calcined. In the event that it is desired to have a metal of Group IA or IIA of the Periodic Table present in the catalyst composite, the third step of the process is effected in a similar manner by subjecting the composite to an impregnation utilizing an aqueous solution containing the desired metal. Examples of salts of these metals which may be employed will include potassium chloride, potassium bromide, potassium iodide, potassium nitrate, potassium sulfate, potassium acetate, potassium propionate, rubidium chloride, rubidium bromide, rubidium iodide, rubidium nitrate, rubidium sulfate, rubidium acetate, rubidium propionate, cesium chloride, cesium bromide, cesium iodide, cesium nitrate, cesium sulfate, cesium acetate, cesium propionate, calcium chloride, barium chloride, barium bromide, barium iodide, barium nitrate, barium sulfate, barium acetate, barium propionate, etc. After allowing the impregnation to proceed for a period of time sufficient to permit the deposition of the desired amount of metal on the catalyst, the composite is recovered, dried and calcined at a temperature within the range hereinbefore set forth, and recovered.

The thus-formed composite containing a noble metal may then be further impregnated with an aqueous solution of a cerium compound. In a similar manner to that hereinbefore described, the amount of soluble salts such as cerium nitrate, cerium oxalate, cerium acetate, cerium chloride, etc. will be present in the solution sufficient so that the finished catalytic composition will contain the desired amount of the metals. After allowing the impregnation to proceed for a predetermined period of time, the composite is recovered, dried, and calcined at a temperature within the range hereinbefore set forth in an air or air/steam atmosphere, following which it is recovered for use in the oxidation portion of the process of the present invention.

It is also contemplated that the preparation of the selective oxidation catalyst may be prepared by coimpregnating the noble metal of Group VIII of the Periodic Table, the metal of Group IVA of the Periodic Table, and if so desired, the metal of Group IA or IIA of the Periodic Table on the solid support. When such a type of preparation is employed, the solid support, such as alumina, is impregnated with an aqueous solution containing salts of the noble metal and the Group IVA metal along with, if so desired, the alkali metal or alkaline earth metal in a manner similar to that hereinbefore set forth. After allowing the impregnation to proceed for a predetermined period of time, the composite is recovered, dried and calcined at a temperature within the range hereinbefore set forth in an air or air/steam atmosphere, following which it is recovered for use in the oxidation portion of the process of the present invention.

Some specific examples of selective oxidation catalytic compositions of matter which may be used in the process of the present invention comprise, as hereinbefore set forth, the noble metals of Group VIII, a metal of Group IA or IIA, a metal of Group IVA, composited on a theta or alpha-alumina possessing the aforementioned physical properties and which has been calcined at a temperature within the ranges hereinbefore set forth. These examples will include platinum, germanium and lithium composited on cerium-containing alumina, palladium, germanium and potassium composited on cerium-containing alumina, rhodium, germanium and potassium composited on cerium-containing alumina, platinum, tin and potassium composited on cerium-containing alumina, palladium, tin and potassium composited on cerium-containing alumina, rhodium, tin and potassium composited on cerium-containing alumina, platinum, germanium and cesium composited on cerium-containing alumina, palladium, germanium and cesium composited on cerium-containing alumina, rhodium, germanium and cesium composited on cerium-containing alumina, platinum, tin and cesium composited on cerium-containing alumina, palladium, tin and cesium composited on cerium-containing alumina, rhodium, tin and cesium composited on cerium-containing alumina, platinum, germanium and barium composited on cerium-containing alumina, palladium, germanium and barium composited on cerium-containing alumina, rhodium, germanium and barium composited on cerium-containing alumina, platinum, tin and barium composited on cerium-containing alumina, palladium, tin and barium composited on cerium-containing alumina, rhodium, tin and barium composited on cerium-containing alumina, platinum, lead and potassium composited on cerium-containing alumina, palladium, lead and potassium composited on cerium-containing alumina, rhodium, lead and potassium composited on cerium-containing alumina, etc. It is to be understood that the above-enumerated catalysts are only representative of the selective oxidation composites which may be used in the process of this invention, and that said invention is not necessarily limited thereto. By utilizing a selective oxidative catalytic composition of matter in a process which involves the dehydrogenation of dehydrogenatable hydrocarbons, it is possible to obtain a process which, in addition to obtaining a desirable and commercially attractive yield of dehydrogenation products, also permits the operation of the process in an economically viable manner due to the catalytic stability of the catalyst under the relatively harsh and stringent operating conditions such as high temperature and high concentration of steam at which the process is operated.

By utilizing the particular alumina support upon which the catalytic metals are impregnated, it is possible to obtain a catalyst which exhibits the desired characteristics of stability and activity which is in contradistinction to prior art types of oxidative catalysts which cannot produce the desired stability exhibited by the present catalysts, and therefore cannot survive in use for a long period of time. This relatively short life of a catalyst discourages the commercial use of such catalysts as unattractive due to the necessity of having to replace or regenerate the catalyst after a short interval of operating time has elapsed. In addition, the catalysts of the present invention also exhibit a definite activity for the selective oxidation of hydrogen rather than a tendency for the oxidation of the dehydrogenated products or unreacted hydrocarbons.

The following examples are given for purposes of illustrating the selective oxidation catalyst of the present invention as well as to a process utilizing the selective oxidation catalyst in said process. However, it is to be understood that these examples are merely illustrative in nature and that the present process is not necessarily limited thereto.

EXAMPLE I:

A catalyst base for the selective oxidation catalyst of the present invention was prepared by placing a Boehmite powder which possessed an Apparent Bulk Density (ABD) of 0.36 g/cc, a surface area of 292 $m^2/g$ and a pore volume of 0.78 cc/g in a mixer. A solution of 37.0 g of nitric acid was added to a sufficient amount of water to form a solution which contained 2.17 wt. % of nitric acid. The solution was then added to the Boehmite powder and admixed. After a period of 6 minutes of stirring, the resultant dough was recovered and extruded.

The extrudate powder was dried for a period of 3 hours at a temperature of 100° C. in a forced draft oven. The extrudate was then precalcined by raising the temperature from ambient to 350° C. during a period of 1 hour in an atmosphere of flowing air which was passed over the extrudate at a rate of 2,000 cc/min. The temperature was maintained at this level for an additional period of 1 hour and thereafter increased to 600° C. during a one-hour period. After maintaining the temperature at 600° C. for an additional period of 3 hours, the extrudate was allowed to cool to ambient temperature in a flowing air atmosphere and recovered. A high temperature calcination was then effected by raising the temperature of the oven from ambient to 1330° C. during a period of 10 hours. The temperature was maintained at this level for an additional period of 3 hours and thereafter the extrudate was allowed to cool.

The extrudate formed according to the above paragraph was then impregnated in the following manner. A solution of chloroplatinic acid was charged to a flask in an amount sufficient to afford 0.4 wt. % platinum based on the weight of the calcined support. In addition, a lithium nitrate solution was also charged to the flask in an amount sufficient to afford 0.2 wt. % of lithium based on the weight of the calcined support. A third solution of cerium nitrate was also added to afford 0.3 weight % of cerium based on the weight of the calcined support. Nitric acid was added in an amount sufficient to afford 16.4 wt. % nitric acid, again based on the weight of the calcined support, and a sufficient amount of deionized water was added to the flask to afford an impregnate solution/calcined support ratio of 1/1 volume/volume. Thereafter a sufficient amount of tin chloride was added to the solution to afford 0.5 weight % tin based upon the weight of the calcined support. The impregnating solution and the calcined support were then placed in a rotary evaporator and subjected to a nitrogen purge at a rate of 1,000 cc/min while cold rolling the mixture for a period of 15 minutes. Upon completion of the cold rolling step, steam was charged to the evaporator jacket and the evaporation of the liquid solution was allowed to proceed until the presence of moisture was not detectable at the mouth of the evaporator.

The catalyst system was then dried in a forced draft oven at a temperature of 150° C. for 2 hours and thereafter calcined. The calcination was effected by raising the heat of the oven from ambient to 650° C. in a stream of air at a rate of 0.5 L/min. Upon attaining the desired temperature, the air which was passed over the catalyst bed was pretreated, the passage through water which was heated to a temperature of 65° C., the temperature and air/steam stream were maintained thereat for a period of 2 hours. At the end of this time, upon completion of the steaming step, the temperature was still maintained at 650° C. while passing only air over the bed for a period of 1 hour. Thereafter the catalyst system was cooled to ambient temperature and recovered. The finished catalyst (A) contained 0.369 weight % platinum, 0.527 weight % tin, 0.195 weight % lithium and 0.289 weight % cerium based upon the support.

A second catalyst, B, was prepared in an identical manner to the catalyst A except that cerium was not incorporated into the support. The finished catalyst contained 0.402 weight % platinum, 0.32 weight % tin, and 0.195 weight % lithium based upon the support.

EXAMPLE II

The catalysts which were prepared according to the above examples were evaluated for conversion of ethylbenzene to styrene with regard to catalyst activity and selectivity for oxygen reacting with hydrogen to form water. The catalysts were loaded into a $\frac{7}{8}''$ inner diameter stainless steel reactor having a 10" long, $\frac{1}{2}''$ diameter base for the catalyst loading. The reactor was heated to an inlet temperature required to achieve a 600° C. maximum catalyst temperature and a feedstock comprising a mixture of ethylbenzene, styrene, steam, hydrogen, oxygen, and nitrogen which simulated a product stream at about a 60% ethylbenzene conversion from a second dehydrogenation catalyst bed of a three dehydrogenation catalyst bed reactor system having an oxidation catalyst bed position between the dehydrogenation catalyst beds was fed to the reactor. The feedstream was passed over the oxidation catalyst bed at the aforesaid inlet temperature and at a reactor outlet pressure of 0.7 atmospheres (0.709 kPa). The hydrocarbon feed was maintained at a Liquid Hourly Space Velocity of 35 hrs$^{-1}$. The molar feed ratio of ethylbenzene and styrene/$H_2O$/$H_2$/$O_2$/$N_2$ equalled 1/9/0.45/0.13/1. In addition, the inlet temperature in the catalyst bed was controlled in order to maintain a maximum temperature of 600° C. in the reactor. The concentration of air at the inlet of the reactor was held constant in order that the activity for oxygen conversion could be measured at a constant GHSV of oxygen.

The amount of catalyst used in each test was equivalent, 12.0 g of catalyst A and 12.0 g of catalyst B.

The most important criteria for catalyst activity is the ability of the catalyst to convert oxygen, defined as oxygen conversion and determined by measuring the concentration of oxygen at the inlet and outlet of the reactor.

The results of the selective oxidation tests when employing the two catalysts are set forth in the tables below. In these tables, the catalyst designated A is the cerium-containing catalyst and catalyst B is the reference catalyst which does not contain cerium.

TABLE 1

| Hours On-Stream | Oxygen Conversion, % | |
|---|---|---|
| | A | B |
| 3 | 96.5 | 92.9 |
| 6 | 96.7 | 92.5 |
| 9 | 96.7 | 91.8 |
| 12 | 95.7 | 91.9 |
| 15 | 96.7 | 91.9 |
| 18 | 96.0 | 91.7 |
| 21 | 96.0 | 91.2 |
| 24 | 97.7 | 91.5 |

It is noted from the above table that the oxygen conversion is significantly greater for Catalyst A, the catalyst which contains cerium, as compared with Catalyst B. Therefore, the cerium-containing catalyst (A) possesses higher activity for the desired reaction which is the oxidation of hydrogen.

TABLE 2

| Hours On-Stream | Reactor Inlet Temperature, °C. | |
|---|---|---|
| | A | B |
| 3 | 554 | 559 |
| 6 | 555 | 557 |
| 9 | 554 | 557 |
| 12 | 554 | 556 |
| 15 | 554 | 557 |
| 18 | 554 | 557 |
| 21 | 554 | 556 |
| 24 | 553 | 556 |

It is noted from the above table that the reactor inlet temperature required to achieve a 600° C. maximum temperature is significantly less for the cerium-containing Catalyst A compared to reference Catalyst B, thus indicating that Catalyst A is more active than Catalyst B.

EXAMPLE III

The ability of a catalyst to maintain high activity for oxygen conversion under the hydrothermal aging conditions is an important factor. The catalysts which were prepared according to the above examples were treated under hydrothermal conditions in order that the stability of these catalysts could be determined. The catalysts were loaded in a 2" I.D. quartz tube possessing a 24" long base for catalyst loading. The reactor was heated to an inlet temperature of 800° C. and a feedstock comprising a mixture of steam, nitrogen, and oxygen was fed to the reactor. The feedstream was passed over the oxidation catalyst bed at the aforesaid inlet temperature and a reactor outlet pressure of 1.0 atmosphere. The molar feed ratio of $H_2O$/$N_2$/$O_2$ equalled 1.0/0.2/0.05. The combined feed was maintained at a Gas Hourly Space Velocity of 5,700 hrs$^{-1}$. The catalysts were treated under the hereinbefore set forth conditions for 24 hours. The activity of the aged catalysts was then evaluated as described in Example II. The results are set forth in Table 3 below.

TABLE 3

| Stability of Catalysts A and B | | |
|---|---|---|
| | Oxygen Conversion, % | |
| Hours On-Stream | Catalyst A (Ce) After Aging | Catalyst B After Aging |
| 3 | 86.7 | 84.4 |
| 6 | 85.8 | 79.9 |

TABLE 3-continued

| | Stability of Catalysts A and B | |
|---|---|---|
| | Oxygen Conversion, % | |
| Hours On-Stream | Catalyst A (Ce) After Aging | Catalyst B After Aging |
| 9 | 85.1 | 82.0 |
| 12 | 84.4 | 81.3 |
| 15 | 83.7 | 78.9 |
| 18 | 85.9 | 80.0 |
| 21 | 84.0 | 80.7 |
| 24 | 82.5 | 80.9 |

The above results indicate that Catalyst A, which contains cerium, possesses a higher activity after hydrothermal aging when compared with Catalyst B, which does not contain cerium. The ability to maintain a high activity after hydrothermal aging is an important property of the cerium-containing catalyst inasmuch as it enables one to employ the catalyst in a commercially successful manner for long periods of time. This results in an overall more cost-effective-process compared with catalysts which are not able to maintain high activity after aging.

We claim:

1. In a process for the dehydrogenation of a dehydrogenatable hydrocarbon with separate and intermediate selective oxidation of hydrogen which comprises the steps of:
   (a) contacting said hydrocarbon with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of unconverted hydrocarbons, dehydrogenated hydrocarbons, hydrogen and steam;
   (b) removing said first-reaction dehydrogenation zone effluent from said first-reaction dehydrogenation zone;
   (c) passing said effluent of step (b) to a second-reaction oxidation zone, which is separate and discrete from said first-reaction dehydrogenation zone;
   (d) contacting said first-reaction dehydrogenation zone effluent in said second-reaction oxidation zone with an oxygen-containing gas to selectively oxidize said hydrogen within said first-reaction zone effluent to the substantial exclusion of oxidation of unconverted and dehydrogenated hydrocarbons in the presence of an oxidation catalyst consisting essentially of a Group VIII noble metal, a Group IVA metal and a Group IA or IIA metal composited on a metal oxide support at oxidation conditions wherein the exothermic selective oxidation of said hydrogen provides additional heat and thereby raises the temperature of said unconverted and dehydrogenated hydrocarbons;
   (e) withdrawing said unconverted and dehydrogenated hydrocarbons from said second-reaction oxidation zone having an increased temperature with respect to the temperature of said first-reaction dehydrogenation zone effluent;
   (f) passing said removed second-reaction oxidation zone product stream of step (e) to a third-reaction dehydrogenation zone containing a dehydrogenation catalyst comprising an alkaline metalpromoted iron compound at dehydrogenation conditions to produce dehydrogenated hydrocarbons; and,
   (g) withdrawing and recovering said dehydrogenated hydrocarbons, the improvement which comprises utilizing as said support a cerium-containing alumina.

2. The process as set forth in claim 1 in which said alumina is alpha-alumina.

3. The process as set forth in claim 1 in which said alumina is a mixture of alpha-alumina and theta-alumina.

4. The process as set forth in claim 1 in which said cerium is present in an amount in the range of from about 0.01% to about 5.0% by weight of said support.

5. The process as set forth in claim 1 in which said dehydrogenation conditions and said oxidation conditions include a temperature in the range of from about 500° to about 700° C. and a pressure in the range of from about 0.1013 kPa to about 10.133 kPa.

6. The process as set forth in claim 1 in which said Group VIII noble metal in said oxidation catalyst is selected from the group consisting of platinum, palladium, and rhodium.

7. The process as set forth in claim 6 in which said Group VIII noble metal is present in said oxidation catalyst in an amount in the range of from about 0.01% to about 5% by weight of said catalyst.

8. The process as set forth in claim 1 in which said Group IVA metal which is present in said oxidation catalyst is selected from the group consisting of germanium, lead, and tin.

9. The process as set forth in claim 8 in which said Group IVA metal is present in said oxidation catalyst in an amount in the range of from about 0.01% to about 5% by weight of said catalyst.

10. The process as set forth in claim 1 in which said Group IA or IIA metal which is present in said oxidation catalyst is selected from the group consisting of sodium, potassium, lithium, rubidium, cesium, beryllium, magnesium, calcium, francium, radium, strontium, barium.

11. The process as set forth in claim 10 in which said Group IA or IIA metal is present in said oxidation catalyst in an amount in the range of from about 0.01% to about 10% by weight of said catalyst.

12. The process as set forth in claim 1 in which said oxygen-containing gas is oxygen.

13. The process as set forth in claim 1 in which said oxygen-containing gas is air.

14. The process as set forth in claim 1 in which said alkaline metal in said dehydrogenation catalyst is selected from the group consisting of Group IA and Group IIA of the Periodic Table.

15. The process as set forth in claim 1 in which said dehydrogenation catalyst contains an oxide or sulfide of a metal selected from the group consisting of Groups IVB, VB and VIB of the Periodic Table.

16. The process as set forth in claim 1 in which said dehydrogenatable hydrocarbon is ethylbenzene and said dehydrogenated hydrocarbon is styrene.

17. The process as set forth in claim 1 in which said dehydrogenatable hydrocarbon is p-ethyltoluene and said dehydrogenated hydrocarbon is p-methylstyrene.

18. The process as set forth in claim 1 in which said dehydrogenatable hydrocarbon is o-ethyltoluene and said dehydrogenated hydrocarbon is o-methylstyrene.

19. The process as set forth in claim 1 in which said dehydrogenatable hydrocarbon is m-ethyltoluene and said dehydrogenated hydrocarbon is m-methylstyrene.

* * * * *